(12) United States Patent
Jacob et al.

(10) Patent No.: US 11,464,491 B2
(45) Date of Patent: Oct. 11, 2022

(54) SHAPE-BASED GENERATIVE ADVERSARIAL NETWORK FOR SEGMENTATION IN MEDICAL IMAGING

(71) Applicant: Siemens Healthcare GmbH, Erlangen (DE)

(72) Inventors: Athira Jacob, Plainsboro, NJ (US); Tiziano Passerini, Plainsboro, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 87 days.

(21) Appl. No.: 16/885,517

(22) Filed: May 28, 2020

(65) Prior Publication Data

US 2021/0038198 A1 Feb. 11, 2021

(30) Foreign Application Priority Data

Aug. 7, 2019 (EP) .................................... 19190567

(51) Int. Cl.
*G06K 9/00* (2022.01)
*A61B 8/08* (2006.01)
*G06T 7/10* (2017.01)
*G16H 30/40* (2018.01)
*G06N 20/20* (2019.01)
(Continued)

(52) U.S. Cl.
CPC .......... *A61B 8/5215* (2013.01); *G06K 9/6215* (2013.01); *G06K 9/6247* (2013.01); *G06N 3/0454* (2013.01); *G06N 3/088* (2013.01); *G06N 20/20* (2019.01); *G06T 7/0012* (2013.01); *G06T 7/10* (2017.01); *G06T 7/60* (2013.01); *G16H 30/40* (2018.01); *G06T 2207/10132* (2013.01); *G06T 2207/20081* (2013.01); *G06T 2207/20084* (2013.01)

(58) Field of Classification Search
CPC ...... G06F 3/017; G06F 16/9554; G06F 16/51; G06F 16/58; G06K 9/00335; G06K 9/00; G06K 9/00127; G06K 9/4628; G06K 9/6224; G06K 9/00134; G06K 9/0014; G06K 9/00221; G06K 9/00288; G06K 9/00651; G06K 9/228; G06K 9/32; G06K 9/6257; G06K 9/6259; G06K 9/627; G06K 9/6271; G06K 9/6857; G06K 9/726; G06N 3/0454; G06N 3/0472; G06N 3/0481; G06N 3/08
See application file for complete search history.

(56) References Cited

U.S. PATENT DOCUMENTS

2004/0264778 A1* 12/2004 Liang ...................... G06K 9/48
382/203
2019/0066281 A1 2/2019 Zheng et al.

OTHER PUBLICATIONS

Qadir, Polyp Detection and Segmentation using Mask R-CNN: Does a Deeper Feature Extractor CNN Always Perform Better?, May 2019, IEEE (Year: 2019).*

(Continued)

*Primary Examiner* — Alex Kok S Liew

(57) ABSTRACT

For segmentation in medical imaging, a shape generative adversarial network (shape GAN) is used in training. By including shape information in a lower dimensional space than the pixels or voxels of the image space, the network may be trained with a shape loss or optimization. The adversarial loss and the shape loss are used to train the network, so the resulting generator may segment complex shapes in 2D or 3D. Other optimization may be used, such as using a loss in image space.

18 Claims, 3 Drawing Sheets

(51) Int. Cl.
  *G06K 9/62* (2022.01)
  *G06N 3/04* (2006.01)
  *G06N 3/08* (2006.01)
  *G06T 7/00* (2017.01)
  *G06T 7/60* (2017.01)

(56) References Cited

OTHER PUBLICATIONS

Hagos "Fast PET Scan Tumor Segmentation Using Superpixels, Principal Component Analysis and K-Means Clustering," Jan. 2018, MDPI (Year: 2018).*

Karimzadeh, A novel shape-based loss function for machine learning-based seminal organ segmentation in medical imaging, 2022, arXiv (Year: 2022).*

Kang, Ensemble of Instance Segmentation Models for Polyp Segmentation in Colonoscopy Images, Feb. 2019, IEEE Access (Year: 2019).*

Al-Arif, et al.; "Shape-aware deep convolutional neural network for vertebrae segmentation." International Workshop and Challenge on Computational Methods and Clinical Applications in Musculoskeletal Imaging. Springer, Cham, 2017. pp. 1-12.

Al-Arif, et al.; "SPNet: Shape Prediction Using a Fully Convolutional Neural Network." International Conference on Medical Image Computing and Computer-Assisted Intervention. Springer, Cham, 2018. pp. 1-8.

Extended European Search Report (EESR) dated Nov. 6, 2019 in corresponding European Patent Application No. 19190567.8.

Degel, et al.:; "Domain and Geometry Agnostic CNNs for Left Atrium Segmentation in 3D Ultrasound", Cornell University Library, 201 Olin Library Cornell University Ithaca, NY 14853, Apr. 20, 2018 (Apr. 20, 2018).

Milletari, et al.:; "V-Net: Fully Convolutional Neural Networks for Volumetric Medical Image Segmentation", CoRR (ArXiv),vol. abs/1606.04797v1, Jun. 15, 2016 (Jun. 15, 2016), pp. 1-11.

Tuysuzoglu, et al.:; "Deep Adversarial Context-Aware Landmark Detection for Ultrasound Imaging", Sep. 13, 2018 (Sep. 13, 2018), International Conference on Computer Analysis of Images and Patterns. CAIP 2017: Computer Analysis of Images and Patterns; Springer, Berlin, Heidelberg, pp. 151-158.

Tran, et al.:; "Disentangling Geometry and Appearance with Regularised Geometry-Aware Generative Adversarial Networks", International Journal of Computer Vision, Kluwer Academic Publishers, Norwell, US, vol. 127, No. 6, Mar. 2, 2019, pp. 824-844.

Al-Arif, el al.; "SPNet: Shape Prediction Using a Fully Convolutional Neural Network." International Conference on Medical Image Computing and Computer-Assisted Intervention. Springer, Cham, 2018. pp. 1-8.

* cited by examiner

SHAPE-BASED GENERATIVE ADVERSARIAL NETWORK FOR SEGMENTATION IN MEDICAL IMAGING

RELATED CASE

This application claims the benefit of EP 19190567.8, filed on Aug. 7, 2019, which is hereby incorporated by reference in its entirety

BACKGROUND

The present embodiments relate to automated segmentation in medical imaging. Shape is widely used in medical image segmentation algorithms to constrain a segmented region to a class of learned shapes. Traditional segmentation is often based on statistical shape models or level sets. Machine learning-based segmentation may not use shape. Deep learning methods have been used to train a network to segment. The loss function used in the training is based on pixel differences (i.e., the training loss is defined in a pixel-wise manner). This results in the loss of a major piece of usable information. The lack of shape priors often results in incorrect topologies. Some attempts have been made to include shape-based loss terms to the optimization in deep learning problems and to optimize directly in shape space. However, these have been shown to work only for simple, relatively convex shapes in two dimensions (2D) and often fail to converge for more complex, three-dimensional (3D) shapes.

SUMMARY

By way of introduction, the preferred embodiments described below include methods, computer readable media, and systems for segmentation. A shape generative adversarial network (shape GAN) is used in training. By including shape information in a lower dimensional space than the pixels or voxels of the image space, the network may be trained with a shape loss or optimization. By using adversarial training, false shapes are penalized. The adversarial loss and the shape loss are used to train the network, so the resulting generator may segment complex shapes in 2D or 3D. Other optimization may be used, such as using a loss in image space.

In a first aspect, a method is provided for segmentation in a medical imaging system. A medical scanner scans a patient, providing first imaging data representing the patient. An image processor segments an object represented in the first imaging data. The segmentation uses a machine-learned generative network applied to the first imaging data. The machine-learned generative network was adversarially trained with optimization in a shape space. An image of the object based on the segmenting is output on a display.

In one embodiment, an ultrasound scanner scans. Other modalities of scanner may be used, such as a computed tomography system or a magnetic resonance system.

In various embodiments, the segmentation includes applying the machine-learned generative network as an image-to-image convolutional deep learned network; the machine-learned generative network having been trained where the shape space comprised a lower dimensional space from manifold or unsupervised learning, such as the shape space being an eigenmatrix from a principal component analysis of a signed distance function; the machine-learned generative network having been trained where the optimization comprised a first loss in an image space and a second loss in the shape space; the machine-learned generative network trained to output a signed distance per pixel or voxel from a boundary of the object; and/or the machine-learned generative network having been trained with a discriminator using an adversarial loss on a distance per voxel or pixel.

In a further embodiment, shape parameters of the shape space are determined from a distance function output by the machine-learned generative network. The shape parameters are used to classify the object based on a comparison to a distribution of parameters; and/or to indicate a confidence in the segmenting based on a comparison to a distribution of parameters.

In a second aspect, a system is provided for object localization. A medical scanner is configured to scan a patient, resulting in image data representing the patient. An image processor is configured to locate, with a machine-learned image-to-image network, an object represented in the image data. The machine-learned image-to-image network was trained using shape priors. A display is configured to display an image as a function of the located object.

In one embodiment, the machine-learned image-to-image network is configured to output a distance by pixel or voxel from a boundary of the object and was trained with an adversarial loss on the distance. In another embodiment, the shape priors are eigenvalues. The machine-learned image-to-image network was trained with a smooth L1 loss for the eigenvalues.

In another embodiment, the machine-learned image-to-image network was trained using a first loss in image space and second loss in a shape space.

In yet another embodiment, the image processor is configured to determine shape parameters from the image data and use the shape parameters to assist diagnosis. For example, the shape parameters are used detect a characteristic of the object, to identify a similar case, and/or identify a confidence in the location of the object.

In a third aspect, a method is provided for machine training a model for segmentation. A generator is machine trained to output the segmentation based on a shape loss and an adversarial loss. The trained generator is stored.

In a further embodiment, ground truths are generated as distances per voxel or pixel from a boundary of an object. The shape loss is a smooth L1 loss based on shape in the distances and the adversarial loss is of the distances in an image space.

In another embodiment, the machine training includes machine training the generator as a fully convolutional neural network based on the shape loss, the adversarial loss, and an image loss. The shape loss may be based on eigenvalues from a linearization of the segmentation output by the generator.

The present invention is defined by the following claims, and nothing in this section should be taken as a limitation on those claims. Features for one type of claim (e.g., method or system) may be used in another type of claim. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principals of the invention. Moreover, in the figures, like reference numerals designate corresponding parts throughout the different views.

DETAILED DESCRIPTION OF THE DRAWINGS AND PRESENTLY PREFERRED EMBODIMENTS

A shape-based generative adversarial model is provided for medical image segmentation. A shape GAN is trained where the optimization is done in shape space in addition to the image space. Shape priors in the shape GAN allows for segmentation of complex shapes.

In image space, the generator of the model may be trained to output values for pixels or voxels based on a difference function, such as a signed difference function. The difference in location from the boundary of the object is estimated. For adversarial training, the use of the difference, such as the signed difference, helps maintain the fidelity of the anatomical shape, allowing training for complex anatomies. The discriminator in adversarial training influences learning the shape prior, as the discriminator penalizes 'false' shapes. The use of the discriminator is another incorporation of shape prior information in addition to optimization in shape space for the generator.

Various loss functions may be used. For the loss in the shape space, a smooth L1 loss is used as the loss function for the shape parameters, such as eigenvalues, instead of L2 loss. Smooth L1 loss stabilizes the network numerically, enabling training with larger images and volumes. Smooth L1 loss may also be used in the image space. Using image based smooth L1 loss speeds up convergence of the network.

In application, the parameters in shape space may serve as a 'marker' for diagnostics. The shape space acts as a low dimensional feature space capturing anatomical and functional characteristics. The shape space parameters for a given scan of a patient may be used for detecting anomalies, sub-par segmentations, pathologies, demographic groups, or other classification. The classification may allow the use of specifically tuned algorithms for segmentation or other diagnostic assistance. The shape parameters may be used as a similarity measure, enabling comparison to similar cases, may be used to identify unusual objects for augmenting training data, and/or may be used to recognize subjects that require the use of alternate algorithms or expert opinions.

Figure 1:
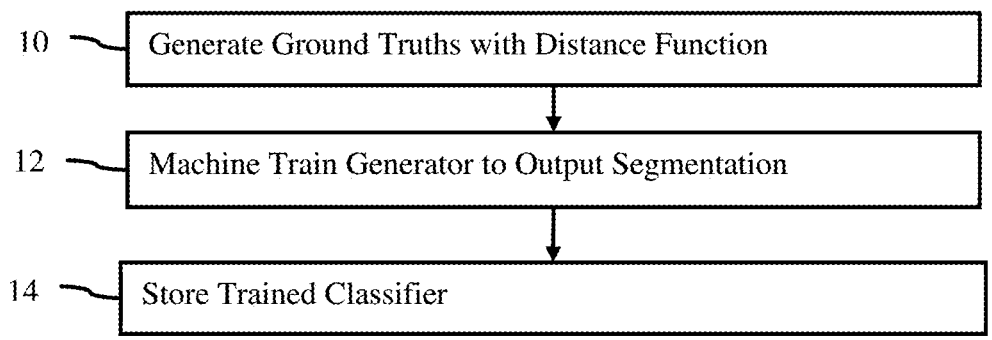
FIG. 1 is a flow chart diagram of one embodiment of a method for training for segmentation using a shape GAN.

FIG. 1 is a flow chart of one embodiment of a method for machine training a model for segmentation. A shape GAN is trained to so that the generator is trained to segment. Due to the use of optimization in shape space, the generator of the shape GAN may be trained to segment complex shapes in 2D or 3D.

Figure 3:
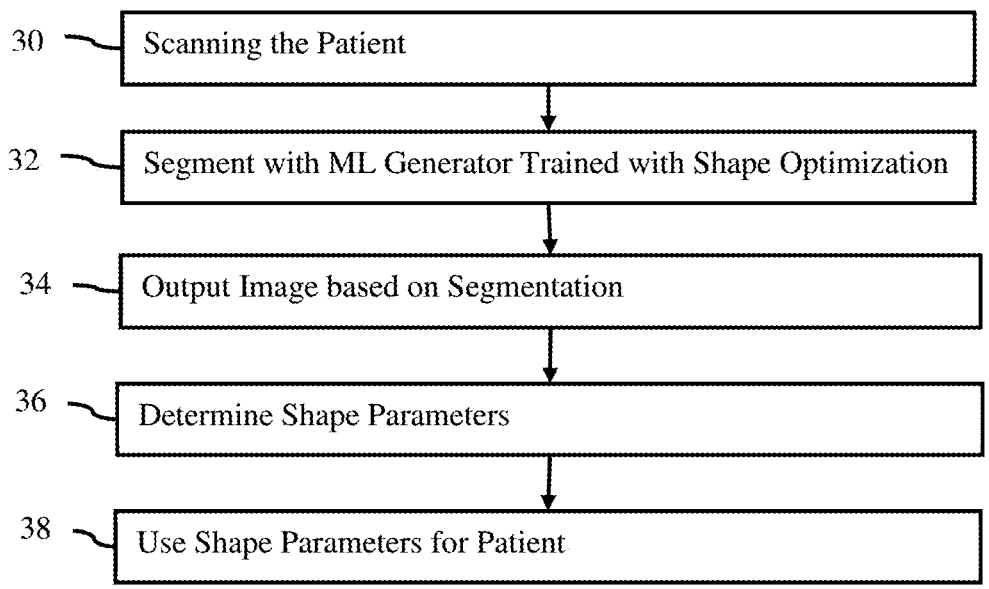
FIG. 3 is a flow chart diagram of one embodiment of a method for segmentation with an adversarially trained generator.
Figure 4:
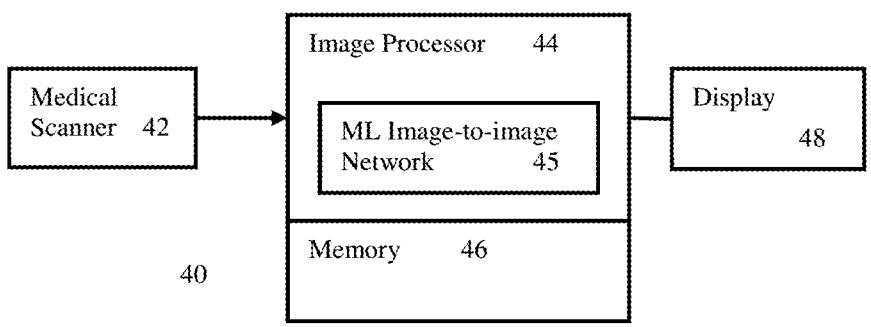
FIG. 4 is a block diagram of one embodiment of a system for segmentation.

The method is implemented by the system of FIG. 4, a workstation, a server, a computer, or other image processor. While FIG. 1 is directed to training, the resulting machine-learned generator may be used by an image processor implementing act 32 of FIG. 3 to segment for a given patient.

The acts are performed in the order shown (top to bottom or numerical) or other orders. Additional, different, or fewer acts may be provided. For example, additional inputs (e.g., patient characteristics, clinical measurements, patient attributes, and/or genomics) may be provided for training.

Ground truth data is obtained for training. The ground truth data is obtained by loading from or accessing memory. Alternatively, the ground truth data is received over a computer network.

For training for segmentation, the ground truth data is segmentations based on imaging data. The training learns to relate an input feature vector to the ground truth segmentation. Where deep learning is used, the input feature vector is the imaging data with or without other information. For other types of machine learning, the input feature vector is information derived from the imaging data, such as Haar wavelets, steerable features, or values calculated from a Hessian matrix.

The ground truth segmentation may be different than image data annotated with the object. In act 10, the ground truth is generated with a distance function. The ground truth location of the boundary of the segmented object is used to generate a ground truth segmentation using a distance function. The ground truth is provided in image space, so provides values for different locations in 2D or 3D. For each location, the distance function is applied to determine the value. The distribution of values provides the segmentation or ground truth.

Any distance function may be used. In one embodiment, a signed distance function (SDF) is used. Locations on one side or within a boundary of an object are assigned one sign (e.g., positive), and locations on another side or outside the boundary of the object are assigned another sign (e.g., negative). Any mapping of distance to magnitude may be used, such as a linear, non-linear, or exponential mapping where lower values are used for locations further away from the boundary.

The distance function may be decomposed into two outputs: a distance function and a level set, where inside pixels are labeled −1, outside is labeled 1 and the contour is labeled 0. The generator is trained to predict two outputs (e.g., distance and level set), which together define the segmented object. A discriminator may be trained on both output together, or separately, to learn shape information during training. Other outputs or combinations of outputs may be used.

For each ground truth sample, the corresponding image data is obtained as training data or samples. Image data is data representing objects or patients, which data may be used to generate an image. The image data may be scan data prior to formatting for display, such as scan data in a scan format different than the display format. The image data may be red, green, blue (RGB) data formatted for display but not displayed or previously displayed. For each ground truth, a corresponding set of image data is provided. Tens, hundreds, or thousands of samples and corresponding ground truths are gathered.

In act 12, a machine (e.g., processor, computer, server, or image processor) machine trains a generator to output a segmentation. Any type of machine training and corresponding classifier may be trained. The machine-trained classifier is any one or more classifiers. A single class or binary classifier, collection of different classifiers, cascaded classifiers, hierarchal classifier, multi-class classifier, model-based classifier, classifier based on machine learning, or combinations thereof may be used. Multi-class classifiers include CART, K-nearest neighbors, neural network (e.g., multi-layer perceptron), mixture models, or others. A probabilistic boosting tree may be used. Error-correcting output code (ECOC) may be used. Deep learning or deep reinforcement learning may be used to detect and segment.

In one embodiment, a neural network is trained using deep learning. Deep adversarial architectures may be used to improve the performance of the segmentation. The machine (e.g., image processor) learns to identify locations of an object based on the input. In an iterative process, the training determines values for filter kernels, node values, weights, and/or other learnable parameters of the generator that relate the input vector to the desired output (i.e., ground truth).

The model is trained to segment any object. For example, an organ is segmented, such as identifying locations of the liver as opposed to other tissue. As another example, an invasive object is identified, such as locating a stent or catheter. Landmarks (e.g., vessel in a kidney) and/or parts (e.g., valve, heart chamber, or vessel bifurcation) may be segmented. The training uses samples from the database, such as samples of scans of patients, and ground truth for the segmentations from those scans to train the model.

Any machine-learned generative network may be used, such as a fully convolutional neural network. For example, the generative network is an image-to-image convolutional deep-learned network. As another example, an encoder-decoder pair is used. In yet another example, a UNet is used with or without skip connections. Other neural networks may be used with or without convolution. The generator receives an image as input and learns to generate a synthetic image as output.

The generator encodes the imaging data to a few independent latent variables and generates synthetic data by sampling the latent variables. In deep learning, the latent variables are learned by machine training. The generative network returns a prior log-likelihood and is implemented as a piecewise-differentiable function, such as used in deep learning. For example, the generative network is a deep-learned model using restricted Boltzmann machines, deep belief network, neural autoregressive density estimators, variational auto-encoders, extensions thereof, or other deep learning approaches for generative modeling. In one embodiment, the trained deep generative network is a deep neural network with a set of j convolutional layers and k fully connected layers, each followed by a non-linear activation function, a set of pooling layers for features reduction, and a set of upscaling layers for image generation. There are generally two parts in the architecture, one (e.g., encoder) convolving learned filters with increasing abstraction using pooling layers and a following part (e.g., decoder) convolving learned filters with decreasing abstraction using upscaling layers. Any amount of abstraction (feature reduction) and corresponding upscaling may be used. Other layer arrangements may be used. Any number of any type of layers in any arrangement with more or fewer portions may be used.

The input imaging data may be one of a 2D slice, 3D slab, 3D volume, or a 4D volume over time. Any number of output channels may be provided. Each output channel represents a synthetic image.

To train the generator, the log-likelihood of the output is maximized. The generator encodes features (i.e., kernels of the convolution layers) that represent the location or magnitude by location in the images. Since generative training is unsupervised, training does not require matched pairs of good and bad images, which is difficult to acquire on a large scale in a medical setting.

The deep learning for the generator uses a discriminator network. Generative adversarial training is used. The discriminator network is a neural network trained to determine whether the output distances or segmentation are a ground truth (i.e., training data) or synthetically created by the generator. The accuracy of distance or segmentation generation by the generator may be increased using the adversarial training. Using a second network (i.e., discriminator network) to decide between a generated and ground truth distances allows for an improvement in the results of the generator being trained.

Figure 2:
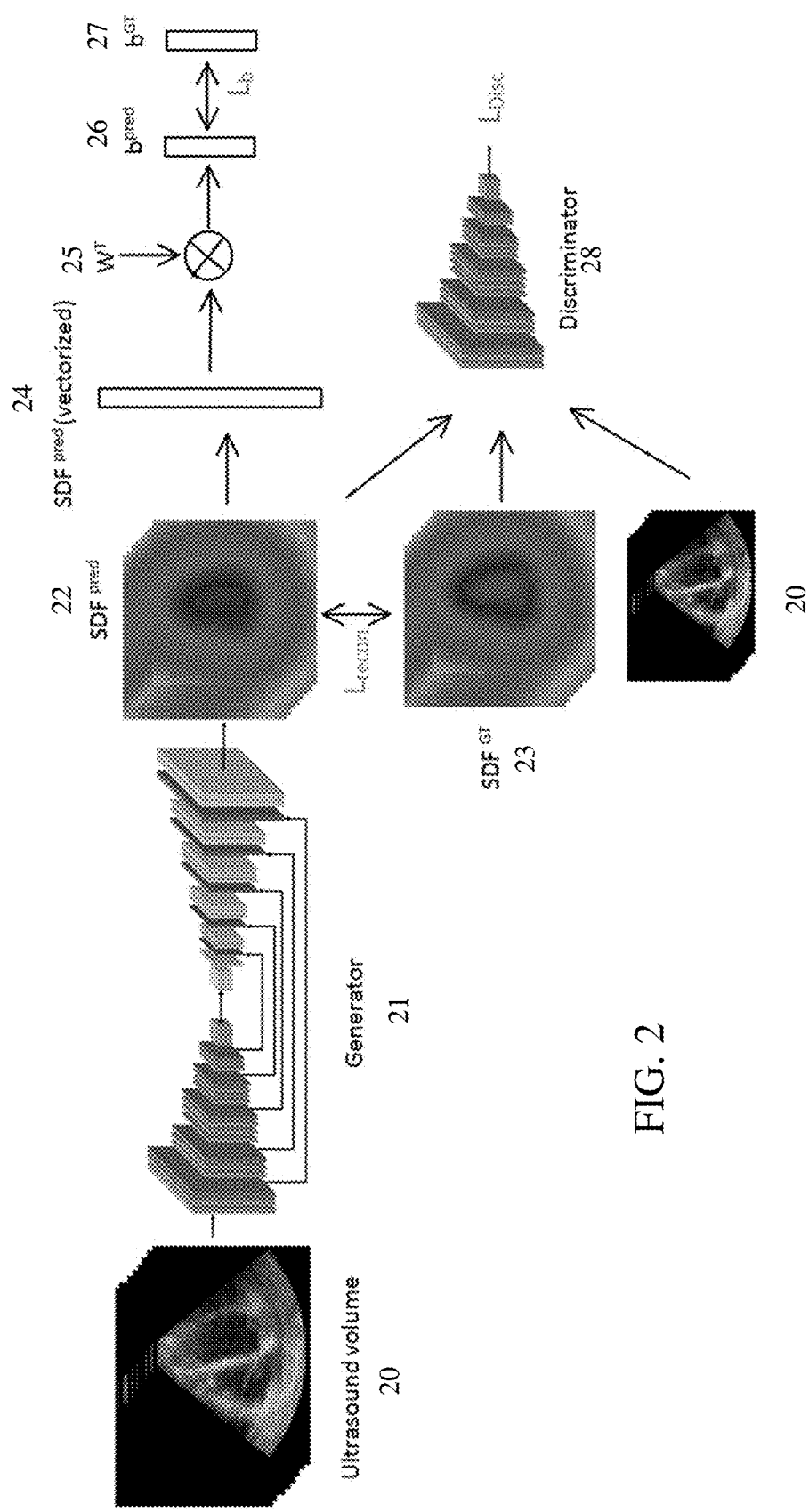
FIG. 2 illustrates an example shape GAN.

FIG. 2 shows an example training arrangement and corresponding networks. In the example of FIG. 2, the training data uses ultrasound volumes 20 as input samples and signed differences by location in 3D as the ground truth 23. 'pred' and 'GT' refer to prediction and ground truth, respectively. The generator 21 is shown as a UNet or encoder-decoder with skip connections and a bottleneck connection.

The output from the generator 21 (i.e., the estimated distances in image space) are used for input to the discriminator network 28 for adversarial training and are used to determine shape parameters in a shape space through manifold 25 for shape priors use in training the generator 21.

The discriminator network 28 includes any layer architecture. In one example, the discriminator network has a similar down sampling architecture portion (e.g., encoder) of convolution layers and pooling layers as the generator 21 but reaches one or more fully connected layers to discriminate between ground truth 23 and generated distances 22. The fully connected layer may be a soft max layer for outputting a binary indication, such as a label as a generated/synthetic or a ground truth.

Additional, different, and/or fewer layers or types of layers may be used for the generator 21 and/or the discriminator network 28. Skip connects (i.e., feeding features forward to non-adjacent layers), feedback, and/or max pooling indices may be used.

The results from training the discriminator network 28 are used to further train the generator 21. An iterative process is used, where both networks communicate results for training each other. The generator 21 uses the output of the discriminator network 28 as an indication of sufficiency (i.e., the discriminator network 28 ability to tell the difference from ground truth is to be minimized). The discriminator network 28 uses the output of the generator 21 as an input to learn to discriminate.

Once trained, the generator 21 is applied without the discriminator network 28 and/or without the manifold 25. The generator 21 outputs distances indicating the segmentation in response to input of the imaging data.

For training, the values of weights, connections, convolution kernels, or other learnable parameters are optimized. Any optimization may be used, such as Adam. Any number of epochs for iterative training may be used.

The optimization operates using one or more losses. The generator 21 is machine trained to output the segmentation (e.g., differences from boundary) based on different losses. In the example of FIG. 2, three losses—reconstruction (image space segmentation) loss ($L_{recon}$), adversarial loss ($L_{Disc}$), and a shape loss ($L_b$)—are used. Additional, different, or fewer losses may be used. For example, the reconstruction loss and/or adversarial losses are not used.

In the optimization, the losses may be combined for optimizing the generator 21. Any combination may be used, such as a weighted sum. The weights are assigned based on an desired or empirical importance between the losses.

The optimization for the shape GAN (e.g., generator 21 and discriminator network 28 with the shape space provided by the manifold 25) is done in the shape space as well as the image space. In one embodiment, the fully convolutional generator 21 predicts values by location of a signed distance function (SDF), where the value of each voxel denotes its shortest, signed distance from the ground truth contour (e.g., boundary of the object). The loss in the image space uses these pixel-by-pixel or voxel-by-voxel distance values. The loss in the shape space uses lower dimensional information (e.g., manifold space) derived from the estimated distances. Other shape-based losses may be used, such as a loss term that directly penalizes deviation from average shape using contour distance measures.

Any loss function may be used. For example, L1 or L2 losses are used. Different loss functions may be used for different losses. In one embodiment, a smooth L1 loss is used for the reconstruction loss in image space and the shape loss in shape space. Huber loss may be used. Any loss for the shape space optimization or the generator reconstruction loss may be used. Mean square error (MSE) may be used for one or both losses. The smooth L1 may help with convergence in the optimization.

For the shape loss, the lower dimensional shape space is used. The lower dimensional space is a lower than the estimated image space. For example, the thousands of distance values (e.g., one for each voxel in 3D) are processed to lower the number of values. This shape space is created from a manifold or unsupervised learning. The manifold 25 or other shape space process may include learnable parameters adjusted during the machine learning. Alternatively, the manifold 25 or other shape space process is set or not variable in the training.

In one embodiment, the shape space is formed as eigenvalues. A principal component analysis (PCA) generates an eigenmatrix of eigenvalues, $b^{pred}$, as the shape space. The shape loss is determined from the eigenvalues as shape parameters. In the example of FIG. 2, the estimated signed distances 22 output by the generator 21 are vectorized. The distances are linearized. Other format changes may be used. The vectorized distances 24 are processed by the manifold 25. For example, the eigenvectors of the matrix of all linearized SDF's of the training data are calculated through Principal Component Analyses (PCA), transforming each data sample using this eigenmatrix (W) to get low dimensional eigenvalues (b) 26 for the sample. The error or shape loss, $L_b$, is calculated within these eigenvalues, $b^{pred}$, 26 relative to eigenvalues, $b^{GT}$, 27 from the ground truth distances 23. The shape loss enables optimization in the lower dimensional shape space rather than higher dimensional image space.

For optimization using the adversarial loss, the discrimination network 28 is trained using different pairs of inputs. To distinguish between generated distances and actual distances, pairs of ground truth distances 23 and generator estimated distances 22 are input as well as pairs of ground truth distances 23 and the original image data 20. Alternatively, just the ground truth distances 23 and the predicted distances 22 are used. The binary output of the discriminator network 28 is used to determine the adversarial loss, $L_{Disc}$. This adversarial loss uses as input the data in the image space, so is related to an image space loss. The adversarial loss is calculated on the SDF 22, 23, so acts as a constraint to maintain the viable shape of the anatomy, allowing prediction of complex anatomies.

The reconstruction loss, $L_{recon}$, is a loss in image space. Differences in the estimated distances 22 from the ground truth distances 23 on a pixel-by-pixel or voxel-by-voxel basis provide the loss, such as using the smooth L1 loss. Including the reconstruction loss in optimization may speed up convergence.

Once trained, the generator 21 has values for the learnable parameters based on the various losses through many iterations using the training data. Due to inclusion of the different losses in optimization, the resulting generator 21 is different than if different losses were used. As a result, the generator 21 operates differently and may provide different results than a generator 21 trained differently.

In act 14 of FIG. 1, the learned or trained generator is stored. The generator is a matrix or architecture with learned values (e.g., convolution kernels) for learnable parameters and set values for other parameters. The machine-learned network is stored for application to an input feature vector for a given unseen patient.

The learned network or generator is stored in the memory with the training data or other memory. For example, copies of the learned network are distributed to or on different medical scanners for use in hospitals or medical practices. As another example, copies are stored in a memory of one or more servers for segmentation as a service or remote segmentation.

FIG. 3 shows a method for segmentation in a medical imaging system. The segmentation uses a machine-learned generative network to locate one or more objects as segmentation. The location or locations of the object or objects are determined.

The method of FIG. 1 is implemented in the order shown (e.g., top to bottom or numerical) or a different order. For example, act 34 may be performed after act 36 and/or as part of act 38.

Additional, different, or fewer acts may be performed. For example, act 30 may be omitted where data is provided from memory or transfer. As another example, acts 36 and/or 28 are not performed.

The method is implemented by a medical imaging system, such as any system for image processing from medical scans. The medical imaging system may be medical diagnostic imaging system, a review station, a workstation, a computer, a picture archiving and communication system (PACS) station, a server, a mobile device, combinations thereof, or another image processor. For example, the system shown in or described for FIG. 4 implements the method, but other systems may be used. A hardware processor of any type of system, interacting with memory (e.g., PACS database or cloud storage), display, and/or medical scanner, may perform the acts.

The acts may be performed automatically. The user causes the patient to be scanned or obtains scan data for the patient from a previous scan. The user may activate the process. Once activated, the object is segmented, and a segmentation image is output to a display or medical record. User input of locations of the anatomy in any of the scan data may be avoided. Due to the generative network for segmentation, there is less likely to be a need for user correction of the segmentation. Some user input may be provided, such as for changing modeling parameter values, correcting detected locations, and/or to confirm accuracy.

In act 30, a medical scanner scans the patient. The medical scanner generates imaging data representing a patient. The image or imaging data is made available by or within the medical scanner. Alternatively, the acquisition is from storage or memory, such as acquiring a previously created dataset from a picture archive and communications system (PACS). A processor may extract the data from a medical records database.

The imaging data may be in any format. While the terms image and imaging are used, the image or imaging data may be in a format prior to actual display of the image. For example, the medical imaging data may be a plurality of scalar values representing different locations in a Cartesian or polar coordinate format different than a display format. As another example, the medical image may be a plurality red, green, blue (e.g., RGB) values output to a display for generating the image in the display format. The medical image may be currently or previously displayed image in the display or another format. The imaging data is a dataset that may be used for imaging, such as scan data or a generated image representing the patient.

Any type of medical imaging data and corresponding medical scanner may be used. In one embodiment, the imaging data is a computed tomography (CT) image acquired with a CT system. For example, a chest CT dataset may be acquired by scanning the lungs. For CT, the raw data from the detector is reconstructed into a three-dimensional representation. As another example, magnetic resonance (MR) data representing a patient is acquired with an MR system. The data is acquired using an imaging sequence for scanning a patient. K-space data representing an interior region of a patient is acquired. Fourier analysis is performed to reconstruct the data from the k-space into a three-dimensional object or image space. In yet another example, the data may be ultrasound data. Beamformers and a transducer array scan a patient acoustically. The polar coordinate data is detected and beamformed into ultrasound data representing the patient.

The medical imaging data represents tissue, fluid, and/or bone structure of the patient. In other embodiments, the medical image represents both function (such as perfusion) as well as structure.

The medical imaging data represents a 2D or 3D region of the patient. For example, the medical imaging data represents an area or slice of the patient as pixel values. As another example, the medical imaging data represents a volume or three-dimensional distribution of voxels. The three-dimensional representation may be formatted as a stack or plurality of two-dimensional planes or slices. Values are provided for each of multiple locations distributed in two or three dimensions. The medical imaging data is acquired as one or more frames of data. The frame of data represents the scan region at a given time or period. The dataset may represent the area or volume over time, such as providing a 4D representation of the patient.

In act 32, an image processor segments an object represented in the imaging data. The segmentation provides an estimate of locations of the object, such as the boundaries or any part of the object. In one embodiment, the segmentation indicates a probability of a boundary of the object, such as an estimate of distances to the boundary where the shortest distances indicate the boundary. Any segmentation identifying locations of a given object or objects may be used. The segmentation distinguishes one object from another represented in the image data.

To segment, the image processor applies the machine-learned generative network to the imaging data. The machine-learned generative model locates the object. The image processor may use the estimated output by the machine-learned generative network to filter, threshold, skeletonize, or further image process to identify the object. Alternatively, the output estimate identifies the object. The distances identify the object.

The application of the generative network results in creation of a synthetic image. The synthetic image may be a spatial distribution of distances representing the proximity to a boarder or contour of the object. In other embodiments, the synthetic image may be the same imaging data but also include a label for the boarder or object. The generative network generates the label. Alternatively, the generative network generates imaging data that includes the labels. The synthetic imaging data may have the label added to the scan data or image, such as having values that highlight the object with particular colors.

The generative model may localize in two or three dimensions. The object may be localized over time in 4D imaging data.

To segment, the imaging data from a scan of a patient is input to the machine-learned generative network. The network, such as a trained image-to-image network learned as a convolutional deep network, generates the segmentation or object location in response to the input. For example, a distribution of signed distances from a boundary per pixel or voxel is generated from the imaging data.

The machine-learned generative network was adversarially trained using a discriminator and discrimination loss. The discriminator is not used in application. The machine-learned generative network was trained with optimization in a shape space. Estimated distances were transformed into shape space as a lower dimensional space using manifold or unsupervised learning. For example, the shape space is an eigenmatrix from a principal component analysis of a signed distance function. The shape space may not be used in application. The optimization to train the generative network used a reconstruction loss in image space, a shape loss in shape space, and an adversarial loss. Once trained, the generative network does not calculate the losses. Instead, the generative network operates as trained through the optimization to generate the synthetic image, such as the signed distances, from input of the image data.

In act 34, the image processor generates an image and causes the image to be output on a display, such as a screen. The image is of the object based on the segmentation. The object only is displayed. Alternatively, the object is highlighted and displayed with other tissue or objects represented in the imaging data. For example, an image is generated from the imaging data. The object is highlighted in the image, such as being colored, displayed with a different brightness, or annotated (labeled with a symbol or alphanumeric text).

The image may be of a 2D plane or area in the patient. The image may be a cross-section through the patient and/or object. Alternatively, the image is a rendering of the three-dimensional distribution to a two-dimensional display, 3D holographic display, an augmented reality display, or virtual reality display.

In act 36, the image processor determines shape parameters of the shape space from a distance function output by the machine-learned generative network. In application, the shape space is used. The estimated distances for a given patient or imaging data are vectorized and transformed to the lower dimensional shape space. The resulting values of the shape parameters (e.g., $b^{pred}$) of a particular patient are used as a specialized marker to give valuable information.

In act 38, the values of the shape parameter for the patient are used to assist diagnosis. The assistance is output to the medical record and/or display. For example, an annotation is added to the image of the segmentation. The annotation indicates the class or other information about the object determined from the values of the shape parameters. A recommendation, such as for further study, confidence level in segmentation, and/or other post-process to apply may be output.

The values of the shape parameters may be compared to a distribution or thresholds to assist in diagnosis. A characteristic of the shape parameters may be calculated and used to assist in diagnosis.

In one embodiment, a 'normal' distribution of $b^{pred}$ is defined by the training set. An average distribution of values of shape parameters is determined from the training data. Distributions of values for different classes may be determined. The distribution for a patient may be compared to one or more normal or reference distributions to determine class membership or similarity.

The object in the patient may be classified based on a comparison of the shape parameters for the patient to a reference distribution of parameters. For example, a $b^{pred}$ that lies on the fringes of the accepted distribution may be considered an anomaly. Thus, the values of the shape parameters may be used to perform anomaly detection on-the-fly. As another example, a sub-par segmentation may be detected by its anomalous values for shape parameters.

In another embodiment, the comparison is used to indicate a confidence in the segmenting. A measure of confidence in the quality of the segmentation is derived, for instance, as a function of the distance of $b^{pred}$ from the mean of the distribution of $b^{pred}$. A lower confidence, associated with a distance in the values of the shape parameters beyond a threshold or thresholds, may be used to automatically invoke expert review or highlighted lower confidence to a radiologist.

Other classification may be performed using the values of the shape parameters. For example, a database of reference hearts and corresponding shape parameter distributions for adult hearts, pediatric hearts, pathological cases, or another class is used to create reference values for shape parameters for the different classes. The eigenvalues of a particular patient are used to slot the patient into these various categories. The classification may then be used to select the machine-learned generative network or other post-processing algorithm based on the category (i.e., different networks for different classes).

The values, $b^{pred}$, of an anomalous patient may be used to augment the training. The training set is improved by finding anomalous patients and including the imaging data as a sample for refining or re-training. The values may be used to find similar cases (values used as a functional and anatomical similarity measure).

The comparison may be by a distance measure, such as average or weighted average difference between values of the shape parameters. Alternatively, a classifier, such as a naïve Bayes classifier, support vector machine, or decision tree, is trained on the shape parameters to explicitly obtain markers for specific anomalies, pathologies, demographic groups, or classes. The trained model outputs the class membership or other information in response to input of the values of the shape parameters.

FIG. 4 shows a system 40 for object localization. The system 40 implements the method of FIG. 1, FIG. 3, or another method. In one embodiment, the system 40 is for application of a machine-learned generative network. Given input imaging data, the system 40 uses the generative network to generate a spatial distribution for localization of an object represented in the imaging data. While the system 40 is described below in the context of application of the previously learned generative network, the system 40 may be used to machine train the generative network using shape loss with or without reconstruction and/or adversarial loss.

The system 40 includes an image processor 44, a memory 46, a display 48, and a medical scanner 42. The image processor 44, memory 46, and display 48 are shown separate from the medical scanner 42, such as being part of a workstation, computer, or server. In alternative embodiments, the image processor 44, memory 46, and/or display 48 are part of the medical scanner 42. In yet other embodiments, the system 40 does not include the medical scanner 42. Additional, different, or fewer components may be used.

The medical scanner 42 is a CT, MR, ultrasound, camera, or other scanners for scanning a lung of a patient. In one embodiment, the medical scanner 42 is a CT system with an x-ray source and detector mounted to a moveable gantry for three-dimensional scanning of the upper torso of the patient. The image processor 44 or other processor of the medical scanner 42 performs computed tomography to determine scalar values for the tissue response to the x-rays in three dimensions. In another embodiment, the medical scanner 42 is an ultrasound scanner. Acoustic energy is generated by a transducer based on transmit beamformer generated electrical signals. A receive beamformer generates samples responsive to echoes from different locations in the patient.

The scan provides the scan data representing the interior of the patient. The medical scanner 42 is configured by user settings or presets to scan the patient, resulting in scan data representing all or at least part of the object in the patient. This imaging data is in any format, such as scalar values distributed in a regular or evenly dispersed 3D grid (i.e., uniform voxels).

The memory 46 is a buffer, cache, RAM, removable media, hard drive, magnetic, optical, database, or other now known or later developed memory. The memory 46 is a single device or group of two or more devices. The memory 46 is shown associated with or part of the image processor 44 but may be outside or remote from other components of the system 40. For example, the memory 46 is a PACS database storing the scan data from the medical scanner 42.

The memory 46 stores the scan or image data, machine-learned generative or image-to-image network 45, and/or information used in image processing to segment the object. For training, the training data (i.e., input feature vectors and ground truth) are stored in the memory 46.

The memory 46 is additionally or alternatively a non-transitory computer readable storage medium with processing instructions. The memory 46 stores data representing instructions executable by the programmed image processor 44. The instructions for implementing the processes, methods and/or techniques discussed herein are provided on computer-readable storage media or memories, such as a cache, buffer, RAM, removable media, hard drive or other computer readable storage media. The machine-learned generative or image-to-image network 45 may be stored as part of instructions for segmentation. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The image processor 44 is a general processor, digital signal processor, three-dimensional data processor, graphics processing unit, application specific integrated circuit, field programmable gate array, digital circuit, analog circuit, artificial intelligence processor, combinations thereof, or other now known or later developed device for applying a machine-learned image-to-image network 45 and/or segmenting. The image processor 44 is a single device, a plurality of devices, or a network. For more than one device, parallel or sequential division of processing may be used. Different devices making up the image processor 44 may perform different functions, such as one processor segmenting by application of the image-to-image network 85 and another processor classifying based on values of shape parameters. In one embodiment, the image processor 44 is a control processor or other processor of a medical diagnostic imaging system (e.g., medical scanner 42). The image processor 44 is a hardware device configured by or operating pursuant to stored instructions, design (e.g., application specific integrated circuit), firmware, or hardware to perform various acts described herein.

The image processor 44 is configured to locate, with a machine-learned image-to-image network, an object represented in the image data. The image data or features derived therefrom are input to the image-to-image network, which generates the segmentation in response. The locations of the object, such as the boundary of the object, are generated by the image-to-image network based on the previous training of the network.

The machine-learned image-to-image network 45 was trained using shape priors. For example, eigenvalues are formed from distances generated by the image-to-image network during training. The machine-learned image-to-image network 45 was trained with a smooth L1 loss for the eigenvalues. Other losses may have been used in the optimization for training, such as a reconstruction loss in image space and/or an adversarial loss.

Based on the past training, the machine-learned image-to-image network 45 is configured to output a distance by pixel or voxel from a boundary of the object. The losses in training are based on the distances.

The image processor 44 may be configured to determine shape space parameters from the image data. For example, the generated image, such as estimated distances or another segmentation, is linearized (e.g., vectorized) and transformed, such as with principal component analysis, other manifold, or an unsupervised model. The transformation determines values for shape parameters.

The image processor 44 may be configured to use the values of the shape space parameters for a given patient to assist in diagnosis, prognosis, and/or treating. For example, the image processor 44 detects a characteristic of the object from the shape space parameters, identifies a similar case from the shape space parameters, and/or identifies a confidence in the location of the object from the shape space parameters.

The image processor 44 may generate an image. The image-to-image network output (e.g., segmentation) is used to generate an image. The image is of the patient with highlighting or relative indication of different parts, such as the object. Any segmentation image or any image representing the object may be generated. The image provides added visualization of the object in addition to an image merely showing the detected tissue (i.e., highlighting or graphic for the segmentation).

The display 48 is a CRT, LCD, plasma, projector, printer, or other output device for showing an image or other output of the image processor 44 and/or medical scanner 42. The display 48 is configured to display an image of the object by an image plane memory storing a created image. Any image that is a function of the located object may be displayed.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for segmentation in a medical imaging system, the method comprising:
    scanning, by a medical scanner, a patient, the scanning providing first imaging data representing the patient;
    segmenting, by an image processor, an object represented in the first imaging data, the segmenting using a machine-learned generative network applied to the first imaging data, the machine-learned generative network having been trained using at least an adversarial loss generated by a machine-learned discriminator network and a shape loss based on eigenvalues from a linearization of a segmentation output by the machine-learned generative network; and
    outputting, on a display, an image of the object based on the segmenting.

2. The method of claim 1 wherein scanning comprises scanning with the medical scanner being an ultrasound system.

3. The method of claim 1 wherein segmenting comprises applying the machine-learned generative network as an image-to-image convolutional deep learned network.

4. The method of claim 1 wherein segmenting comprises segmenting with the machine-learned generative network having been trained where a shape space for the shape loss comprises a lower dimensional space from manifold or unsupervised learning.

5. The method of claim 4 wherein segmenting comprises segmenting with the machine-learned generative network having been trained where the shape space comprised an eigenmatrix from a principal component analysis of a signed distance function.

6. The method of claim 1 wherein segmenting comprises segmenting with the machine-learned generative network having been trained where the optimization further comprised a first loss in an image space.

7. The method of claim 1 wherein segmenting comprises segmenting with the machine-learned generative network trained to output a signed distance per pixel or voxel from a boundary of the object.

8. The method of claim 1 further comprising:
    determining shape parameters in a shape space from a distance function output by the machine-learned generative network; and
    classifying the object based on a comparison of the shape parameters to a distribution of parameters.

9. The method of claim 1 further comprising:
    determining shape parameters in a shape space from a distance function output by the machine-learned generative network; and
    indicating a confidence in the segmenting based on a comparison of the shape parameters to a distribution of parameters.

10. A system for object localization, the system comprising:
    a medical scanner configured to scan a patient, the scan resulting in image data representing the patient;

an image processor configured to locate, with a machine-learned image-to-image network, an object represented in the image data, the machine-learned image-to-image network having been trained using at least an adversarial loss generated by a machine-learned discriminator network and a shape loss based on eigenvalues from a linearization of a segmentation output by the machine-learned image-to-image network; and a display configured to display an image as a function of the located object.

11. The system of claim 10 wherein the machine-learned image-to-image network is configured to output a distance by pixel or voxel from a boundary of the object and was trained with the adversarial loss on the distance.

12. The system of claim 10 wherein the machine-learned image-to-image network was trained with a smooth L1 loss for the eigenvalues.

13. The system of claim 10 wherein the image processor is configured to determine shape parameters from the image data and detect a characteristic of the object from the shape parameters.

14. The system of claim 10 wherein the image processor is configured to determine shape parameters from the image data and identify a similar case from the shape parameters.

15. The system of claim 10 wherein the image processor is configured to determine shape parameters from the image data and identify a confidence in the location of the object from the shape parameters.

16. A method for machine training a model for segmentation, the method comprising:

machine training a generator to output the segmentation based on an adversarial loss generated by a machine-learned discriminator network and a shape loss based on eigenvalues from a linearization of a segmentation output by the generator a; and storing the trained generator.

17. The method of claim 16 further comprising generating ground truths as distances per voxel or pixel from a boundary of an object, wherein the shape loss is a smooth L1 loss based on shape in the distances and the adversarial loss is of the distances in an image space.

18. The method of claim 16 wherein machine training comprises machine training the generator as a fully convolutional neural network based on the shape loss, the adversarial loss, and an image loss.

* * * * *